(12) United States Patent
Cleary et al.

(10) Patent No.: US 11,872,001 B2
(45) Date of Patent: *Jan. 16, 2024

(54) ARTICULATING CAMERA STAND

(71) Applicant: GLOBUS MEDICAL, INC., Audubon, PA (US)

(72) Inventors: David Cleary, Somerville, MA (US); Norbert Johnson, North Andover, MA (US); Kevin Zhang, Medford, MA (US)

(73) Assignee: Globus Medical, Inc., Audubon, PA (US)

( * ) Notice: Subject to any disclaimer, the term of this patent is extended or adjusted under 35 U.S.C. 154(b) by 382 days.

This patent is subject to a terminal disclaimer.

(21) Appl. No.: 17/130,320

(22) Filed: Dec. 22, 2020

(65) Prior Publication Data
US 2021/0106392 A1 Apr. 15, 2021

Related U.S. Application Data

(63) Continuation of application No. 16/243,694, filed on Jan. 9, 2019, now Pat. No. 10,898,283, which is a
(Continued)

(51) Int. Cl.
A61B 34/30 (2016.01)
A61B 50/13 (2016.01)
A61B 34/20 (2016.01)

(52) U.S. Cl.
CPC .............. *A61B 34/30* (2016.02); *A61B 34/20* (2016.02); *A61B 50/13* (2016.02);
(Continued)

(58) Field of Classification Search
CPC ......... A61B 34/30; A61B 34/20; A61B 50/13; A61B 2034/2055; A61B 2034/2057; A61M 2209/084; A61M 2209/086
See application file for complete search history.

(56) References Cited

U.S. PATENT DOCUMENTS 5,117,521 A * 6/1992 Foster .................. A61G 12/008
5/503.1
5,370,111 A 12/1994 Reeder et al.
(Continued)

FOREIGN PATENT DOCUMENTS

EP 2357117 A1 8/2011
JP 2002321625 A 11/2002
(Continued)

*Primary Examiner* — Richard G Louis

(57) ABSTRACT

Devices, systems and methods for detecting a position of an object with a robot surgical system having an articulable, separable camera stand. The surgical robot system may include a robot having a robot base with a robot arm and an end-effector coupled to the robot arm. The end-effector, surgical instruments, the patient, other objects, or any combination thereof, may be tracked via active and/or passive tracking markers. A camera, such as an infrared camera, a bifocal camera or a stereophotogrammetric infrared camera, is mounted on a separable camera stand and is able to detect the tracking markers when in use. Using the camera, the robot determines a position of the object from the tracking markers, which may be a three-dimensional position of the object or the markers. When convenient, the camera base may be assembled into the robot base, e.g., by sliding the camera base into the robot.

18 Claims, 19 Drawing Sheets

Related U.S. Application Data continuation of application No. 15/207,636, filed on Jul. 12, 2016, now Pat. No. 10,206,749.

(52) U.S. Cl.
CPC ............ *A61B 2034/2055* (2016.02); *A61B 2034/2057* (2016.02); *A61M 2209/084* (2013.01); *A61M 2209/086* (2013.01)

(56) References Cited

U.S. PATENT DOCUMENTS

| | | | |
|---|---|---|---|
| 6,073,942 A | 6/2000 | Heneveld, Sr. | |
| 6,698,770 B2 | 3/2004 | Eriksson et al. | |
| 7,311,657 B2 | 12/2007 | Boone et al. | |
| 8,474,794 B2 | 7/2013 | Liljedahl | |
| 8,535,214 B2 | 9/2013 | Chilton, III | |
| 9,097,384 B1 | 8/2015 | Simon et al. | |
| 9,245,406 B2 | 1/2016 | Fitzgerald et al. | |
| 10,105,470 B2 | 10/2018 | Reasoner et al. | |
| 2005/0212233 A1 | 9/2005 | Hall | |
| 2006/0016009 A1 | 1/2006 | Mannix | |
| 2006/0122541 A1* | 6/2006 | Tuma | A61B 5/4528 600/587 |
| 2007/0106128 A1 | 5/2007 | Lavallee | |
| 2012/0289765 A1 | 11/2012 | Kaushansky et al. | |
| 2015/0032164 A1* | 1/2015 | Crawford | A61B 17/7074 606/279 |
| 2015/0224237 A1* | 8/2015 | Reasoner | A61B 50/13 604/320 |

FOREIGN PATENT DOCUMENTS

| | | |
|---|---|---|
| JP | 2010-22505 A | 2/2010 |
| JP | 2015-532194 A | 11/2015 |

\* cited by examiner

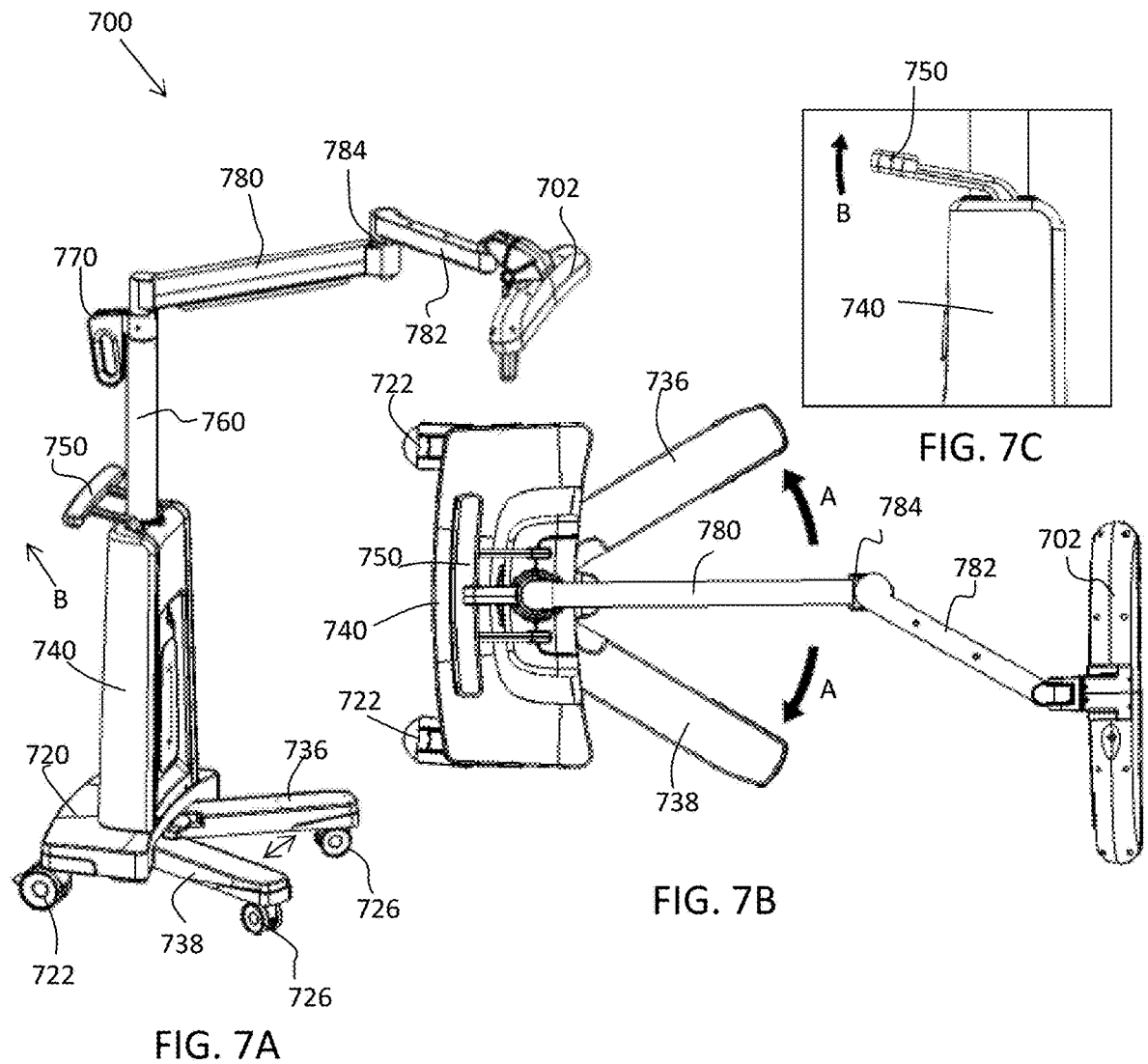

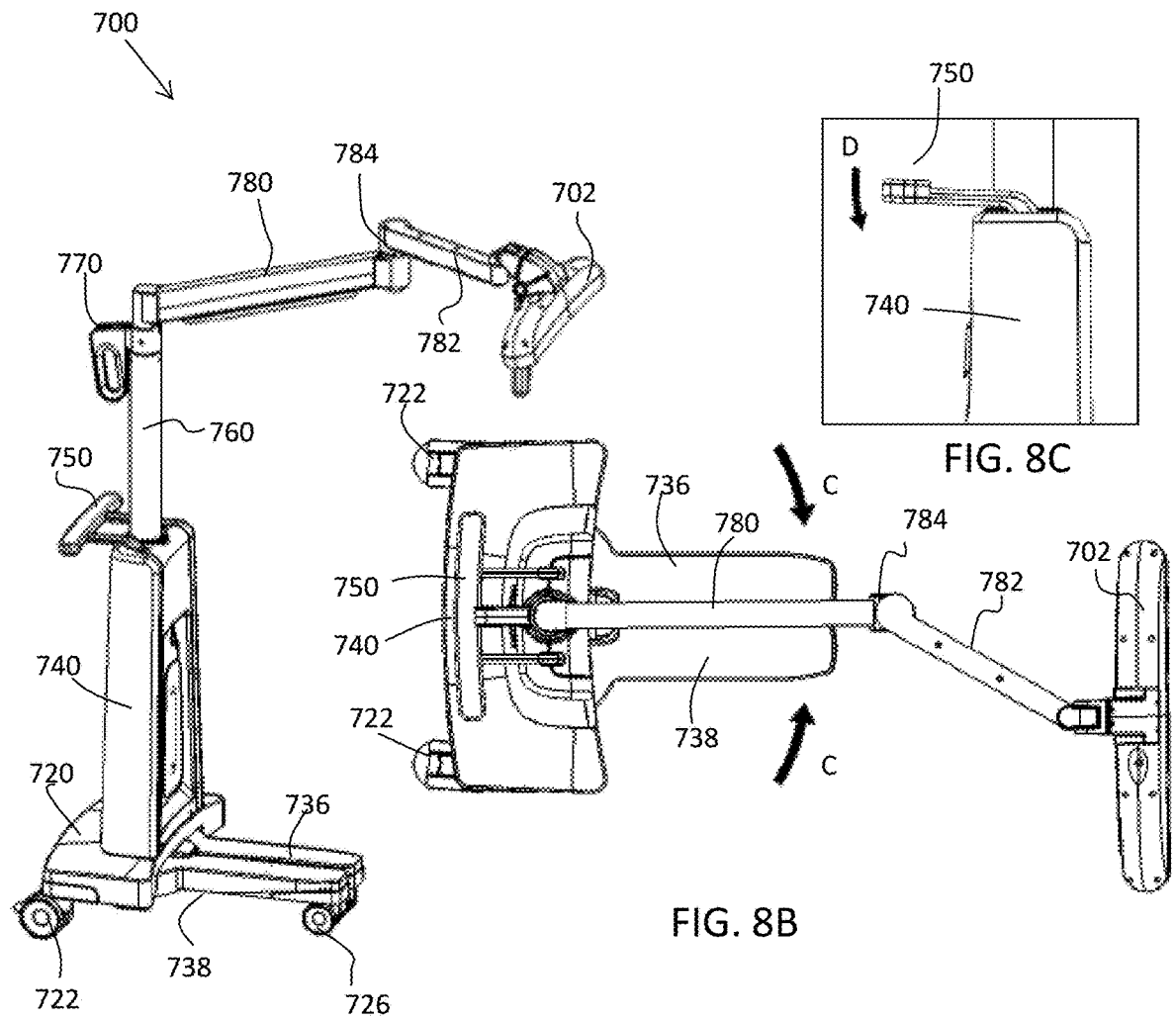

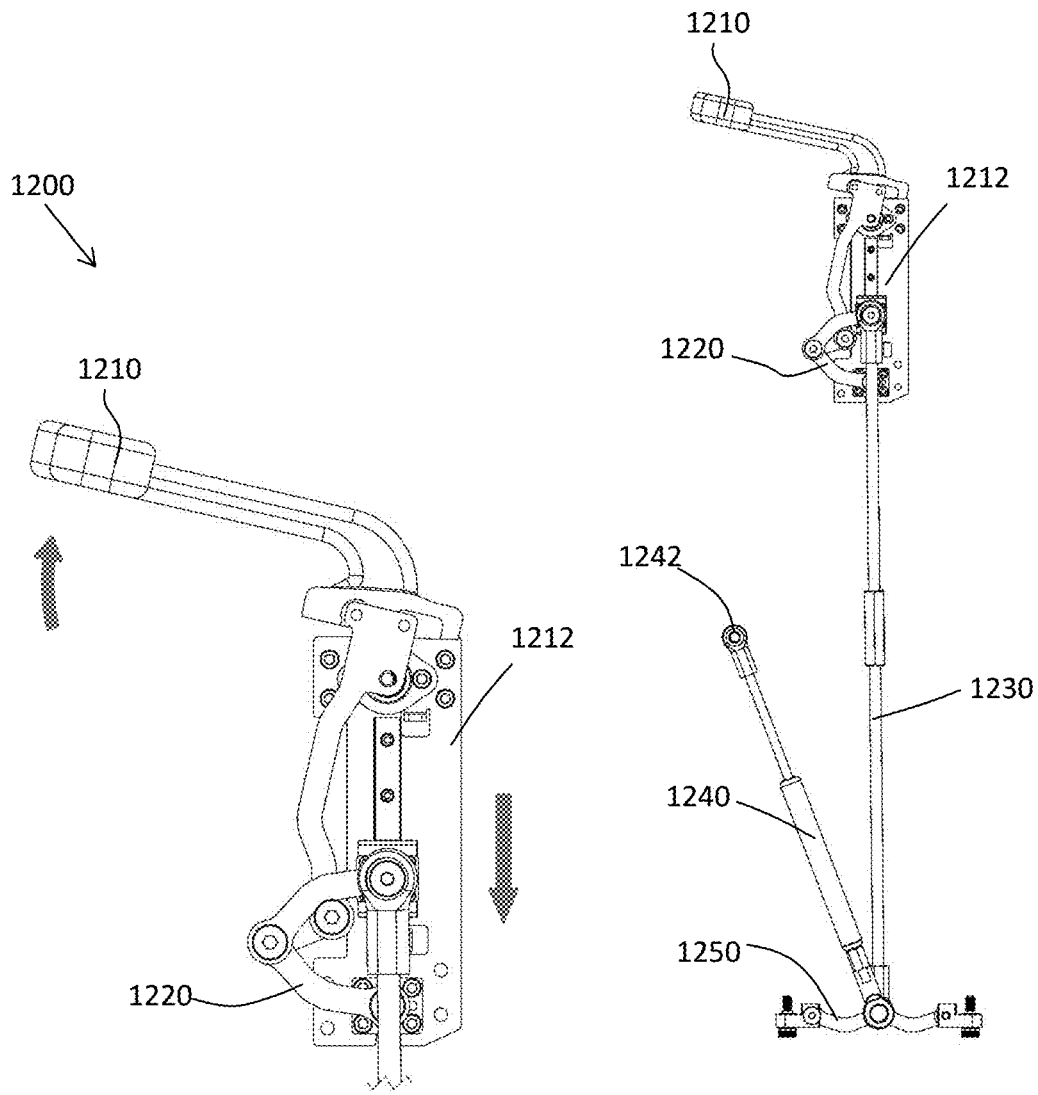
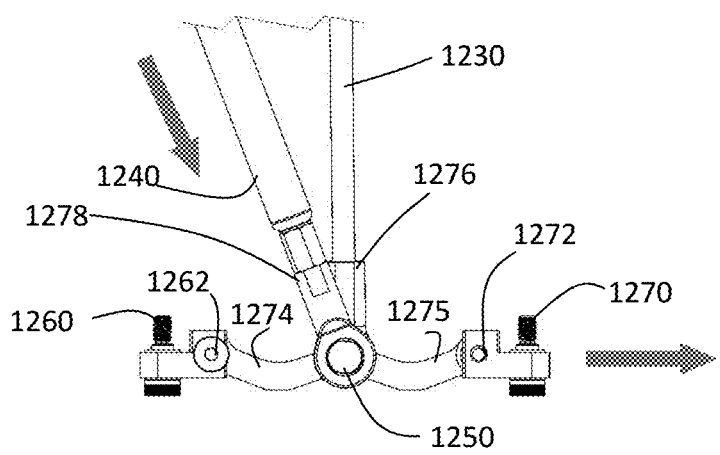
FIG. 12A
FIG. 12B

US 11,872,001 B2

ARTICULATING CAMERA STAND

CROSS REFERENCE TO RELATED APPLICATIONS

This patent application is a continuation of U.S. patent application Ser. No. 16/243,694 filed on Jan. 9, 2019 (published as U.S. Pat. Pub. No. 2019-0142534), which is a continuation of U.S. patent application Ser. No. 15/207,636 filed on Jul. 12, 2016, now U.S. Pat. No. 10,206,749), all of which are incorporated by reference in their entireties herein for all purposes.

FIELD

The present disclosure relates to an articulating camera stand, and in particular, an articulating camera stand that can stand alone during a robot assisted surgery, the articulating camera stand also being capable of assembly to or entry into a surgery-assisting robot.

BACKGROUND

Position recognition systems are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Infrared signal based position recognition systems may use a camera in conjunction with passive and/or active sensors or markers for tracking the objects. In passive sensors or markers, objects to be tracked may include passive sensors, such as reflective spherical balls, which are positioned at strategic locations on the object to be tracked. Infrared transmitters transmit a signal, and the reflective spherical balls reflect the signal to aid in determining the position of the object in 3D. In active sensors or markers, the objects to be tracked include active infrared transmitters, such as light emitting diodes (LEDs), and thus generate their own infrared signals for 3D detection.

With either active or passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

Such robot surgical systems are advantageously used with a dedicated camera system. One disadvantage with the dedicated camera system is that by necessity, the camera should be separate from the robot surgical system in order to give the camera an optimal viewing angle of the surgical procedure. Physical separation is typically achieved by using a separate, independent camera stand, thus allowing flexibility for camera positioning. This requires a considerable amount of space in a relatively crowded area, e.g., an operating theater. Separating the camera stand from the main system or surgical robot can result in logistic challenges, such as storing an additional piece of capital equipment in the hospital, where space is at a premium. Another challenge is transporting an additional piece of capital equipment between procedure rooms, e.g., operating theaters or other locations in which the surgical robot is employed. The ability to reduce the amount of space required for the camera system would be helpful in managing the limited amount of space in an operating theatre.

SUMMARY

To meet this and other needs, devices, systems, and methods for storing and deploying a separate camera with a camera stand in a surgical robot for use in robot-assisted surgeries is disclosed.

One embodiment of the present disclosure is a surgical robot system. The surgical robot system includes a surgical robot having a robot base and a robot arm coupled to the robot base, and a camera stand for mounting a camera, the camera stand comprising a base with casters, a housing and a camera-mounting portion. In this embodiment, the robot is adapted to dock at least a portion of the camera stand within a portion of the robot base, the docked camera stands supported in an elevated position by the robot.

Another embodiment is a surgical robot system. The system includes a surgical robot having a robot base and a robot arm coupled to the robot base, the robot base including a lifting mechanism (e.g., a sloped internal ramp, linear actuator, linkage, or the like), and a camera stand for mounting a camera, the camera stand comprising a base with casters, a housing and a camera-mounting portion, the camera stand also including two legs, each leg configured for mounting the camera stand with the lifting mechanisms of the robot base. In this system, the robot is adapted to dock at least a portion of the camera stand within a portion of the robot base, the docked camera stands supported in an elevated position by the robot.

There are many other embodiments of the disclosures contained herein.

DESCRIPTION OF THE DRAWINGS

FIGS. 7A-7C depict, respectively, front perspective, top and partial side view of another exemplary embodiment of a camera stand according to the present disclosure in a deployed configuration;

FIGS. 8A-8C depict, respectively, front perspective, top and partial side views of the camera stand of FIGS. 7A-7C in a docking configuration and ready for docking to a robot;

FIGS. 12A-12B depict internal details of the dockable, deployable camera stand of FIGS. 10A, 10B and 11, as an operator moves to deploy the camera stand;

DETAILED DESCRIPTION

Figure 1:
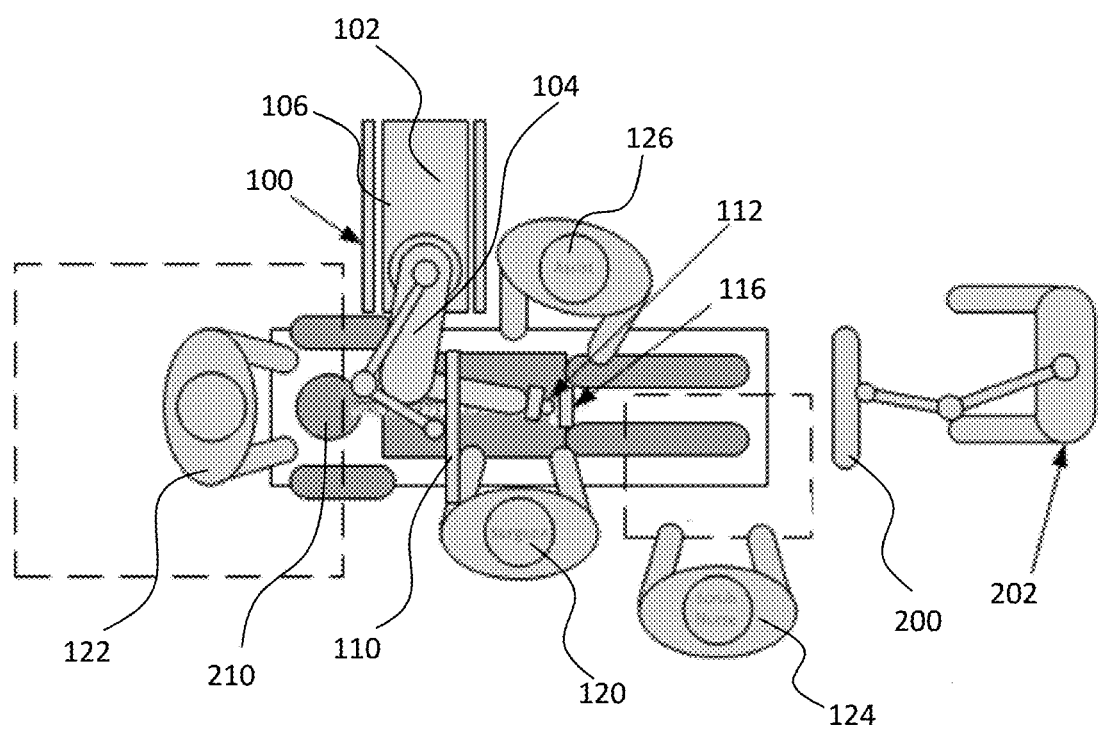
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

This disclosure concerns an articulating camera stand that can be docked with a main system, e.g., a surgical robot, to reduce a footprint of the system during transport and storage. The entire system in the docked configuration can be maneuvered by a single person. A minimal footprint is achieved by configuring the camera stand to interlock with a surgical robot or other main system, such that the two footprints overlap, thereby reducing the footprint added to the surgical robot or other main system. While in the docked position, the wheels or casters of the camera stand are elevated above the floor or ground. This offers improved maneuverability compared to a docked camera stand—robot combination with all wheels or casters on the ground. Lifting the casters off the floor also improves the ease of rolling the casters over uneven horizontal surfaces, e.g., thresholds. In embodiments, the camera stand can be docked to the surgical robot or deployed from the surgical robot without tools. In embodiments, when the camera stand is undocked, the articulating or rotatable legs automatically go to a deployed position in which the legs are spread apart for stability. This gives the camera stand the stability and the flexibility to position the camera as desired throughout the operating room. For docking, the legs are joined together for mounting to the surgical robot or other main system.

Figure 2:
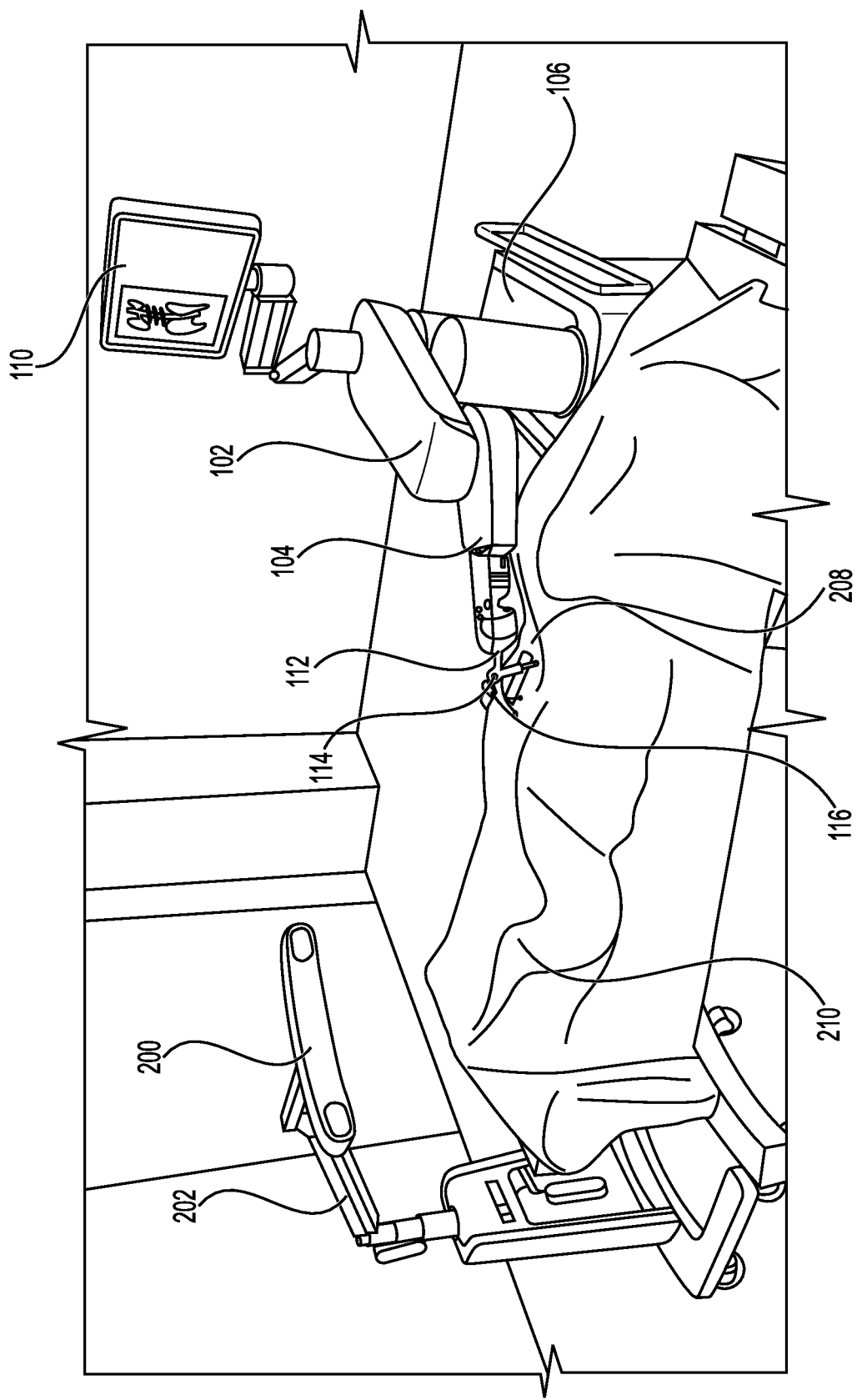
FIG. 2 illustrates the robotic system including positioning of the surgical robot and the camera stand relative to the patient according to one embodiment.

Turning now to the drawings, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which marker(s) are adapted to be secured directly to the patient 210 (e.g., to the bone of the patient 210) or to objects as described herein. The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a holder or a guide tube 114, which is able to receive and orient a surgical instrument (not shown) used to perform surgery on the patient 210. By way of example, the surgical instrument may include one or more of a guide wire, cannula, a retractor, a drill, a reamer, a screw driver, an insertion tool, a removal tool, or the like. As used herein, the term "end-effector" is used interchangeably with the terms "end-effectuator" and "effectuator element." A "surgical instrument" generally describes a device which contacts the patient, while the "end-effector" generally described a physical interface between the "surgical instrument" and the robot arm. Although generally shown with a guide tube 114, it will be appreciated that in some embodiments the end-effector 112 may be replaced with any suitable instrumentation suitable for use in surgery. In some embodiments, end-effector 112 can comprise any known structure for effecting the movement of the surgical instrument in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y- and z-axis, and a Z Frame axis (such that one or more of the Euler Angles (e.g., roll, pitch and yaw) associated with end-effector 112 can be selectively controlled). In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument can be dynamically updated so that surgical robot 102 can be aware of the location of the surgical instrument at all times during the procedure. Consequently, in some exemplary embodiments, surgical robot 102 can move the surgical instrument to the desired position quickly without any further assistance from a physician (unless the physician so desires). In some further embodiments, surgical robot 102 can be configured to correct the path of the surgical instrument if the surgical instrument strays from the selected, preplanned trajectory. In some exemplary embodiments, surgical robot 102 can be configured to permit one or more of stoppage, modification, and manual control of the movement of end-effector 112 and the surgical instrument. Thus, in use, in exemplary embodiments, a physician or other medical professional can operate the system 100 and has the option to stop, modify or manually control the autonomous movement of end-effector 112 and surgical instrument. Further details of surgical robot system 100 including the control and movement of a surgical instrument by surgical robot 102 can be found in co-pending U.S. patent application Ser. No. 13/924,505, which is incorporated herein by reference in its entirety.

The robotic surgical system 100 can comprise one or more tracking markers 118 configured to track the movement of the surgical robot 102, the robot arm 104, end-effector 112, patient 210, and/or the surgical instrument in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools (e.g., a screw driver, dilator, implant inserter, or the like). Thus, the tracking markers 118 enable each of the marked objects (e.g., the end-effector 112, the patient 210, and the surgical tools) to be tracked by the robot 102. In exemplary embodiments, system 100 can use tracking information collected from each of the marked objects to calculate the orientation and location, for example, of the end-effector 112, the surgical instrument (e.g., positioned in the tube 114 of the end-effector 112), and the relative position of the patient 210.

In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument can be found in co-pending U.S. patent application Ser. No. 13/924,505, which is incorporated herein by reference in its entirety.

Exemplary embodiments include one or more markers 118 coupled to the surgical instrument. In exemplary embodiments, these markers 118, for example, coupled to the patient 210 and surgical instruments, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3A:
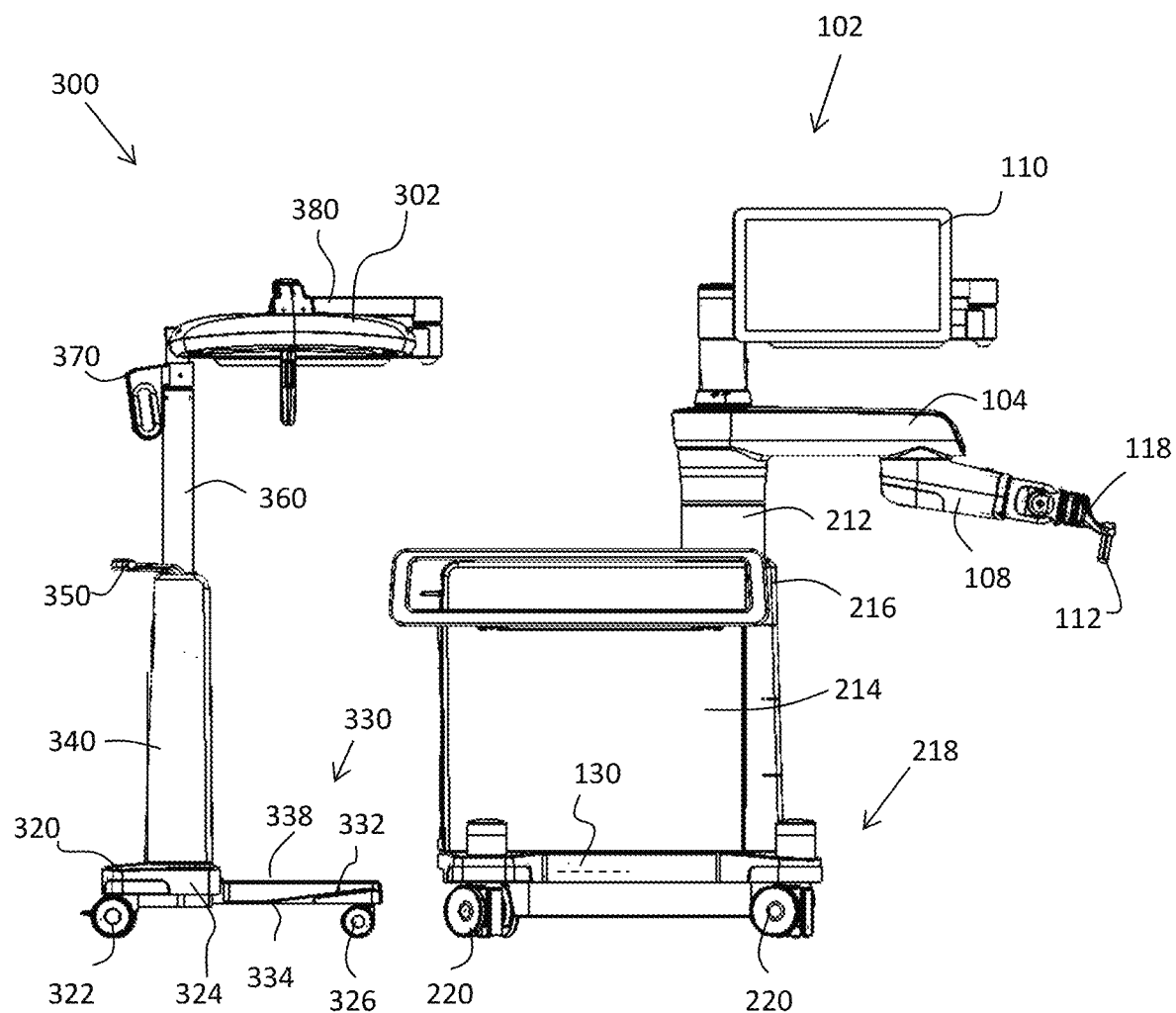
FIG. 3A illustrates a surgical robotic system with a separable, dockable camera stand in accordance with an exemplary embodiment.

A closer view of a surgical robot 102 and a dockable, separable camera stand 300 is depicted in FIG. 3A. In this side view, surgical robot 102 includes a movable, articulable first surgical arm 104, a second, movable, articulable surgical arm 108, and an end effector 112, for example, in the form of a guide tube configured to accept a surgical instrument. The end effector 112 may include one or more tracking markers 118. The surgical robot 102 also includes a vertical column 212, a cabinet 214 and drawer 216, along with a surgical robot base 218, and casters or wheels 220 for mobility.

The surgical robot base 218 includes a lifting mechanism configured to mate with and receive a portion of the camera stand 300. For example, the lifting mechanism may include one or more ramps, one or more linear actuators, one or more linkages, or the like. The lifting mechanism may receive the legs 336, 338 of the camera stand 300 such that the camera stand 300 is docked within a portion of the robot base 218 and the lifting mechanism causes the docked camera stands to remain supported in an elevated position by the robot 102. According to one embodiment shown, the lifting mechanism, shown as a dashed line, is an internal ramp 130. It is understood that some embodiments of the internal ramp 130 include a sloped portion and a level portion, on both sides of the surgical robot base, so that the surgical robot 102 is able to store the camera stand 300 above a level of the floor or ground, as shown below in FIG. 3B.

Camera stand 300 includes a camera 302 mounted to the camera stand 300, and also includes a base 320, rear wheels 322 (only one seen in FIG. 3A), front wheels 326 (only one visible in FIG. 3A), central portion 324, right leg 338 (see left leg 336 in FIG. 6) and ramp 330. Ramp 330 includes a sloped front portion 332 on the right leg, followed by a level portion 334. Camera stand 300 also includes a vertical column portion 360 as well as control handle 370. In embodiments, control handle 370 may be used to control one or more of the vertical extension of vertical column 360, as well as the articulation angles for the horizontal extensions 380 of the camera mount—see FIGS. 7A-7C for better view of these horizontal extensions.

Figure 3B:
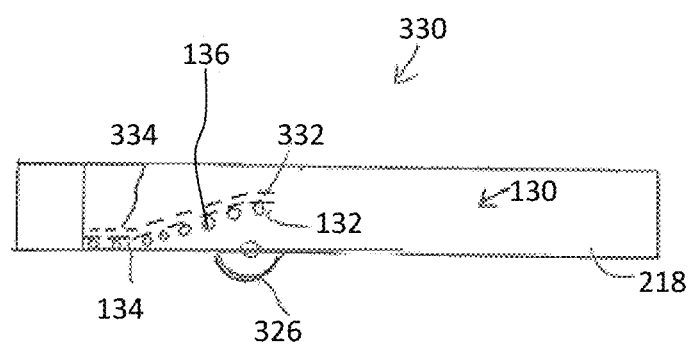
FIG. 3B depicts a partial view of an internal portion of the surgical robot system for docking the camera stand.

Using ramp 330, camera stand 300 may be docked to surgical robot 102, which has a suitable internal docking ramp 130 to accommodate the camera stand. A closer look at the ramp configuration is shown in FIG. 3B as ramp 330. In this illustration, surgical robot internal ramp 330 is shown to include rollers 136 in the form of a sloped portion 132 and a level portion. In FIG. 3B, the camera stand 300 has docked with the surgical robot 102, and the ramp 330 of the camera stand 300, with forward sloped portion 332 and rearward level portion 334, now secures the camera stand 300 to the surgical robot 102. In embodiments, the camera stand 300 is latched to the surgical robot 102 for greater security, as shown below. In FIG. 3B, a front wheel 326 of the mounted or docked camera stand 300 is shown protruding from the base 118 of the surgical robot 102.

Figure 4:
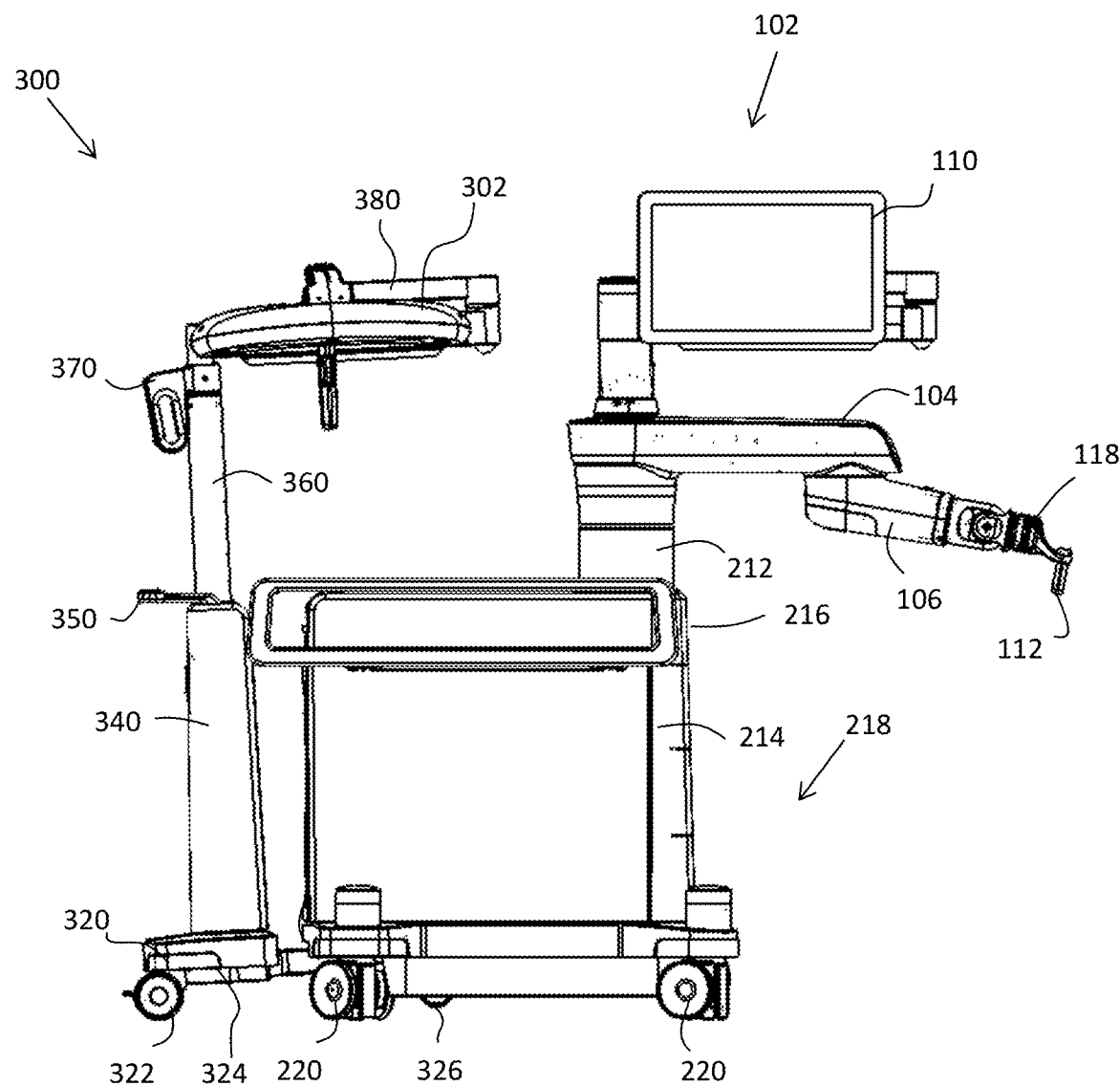
FIGS. 4 and 5 illustrate the docking of the camera stand to the surgical robot in accordance with an exemplary embodiment.
Figure 5:
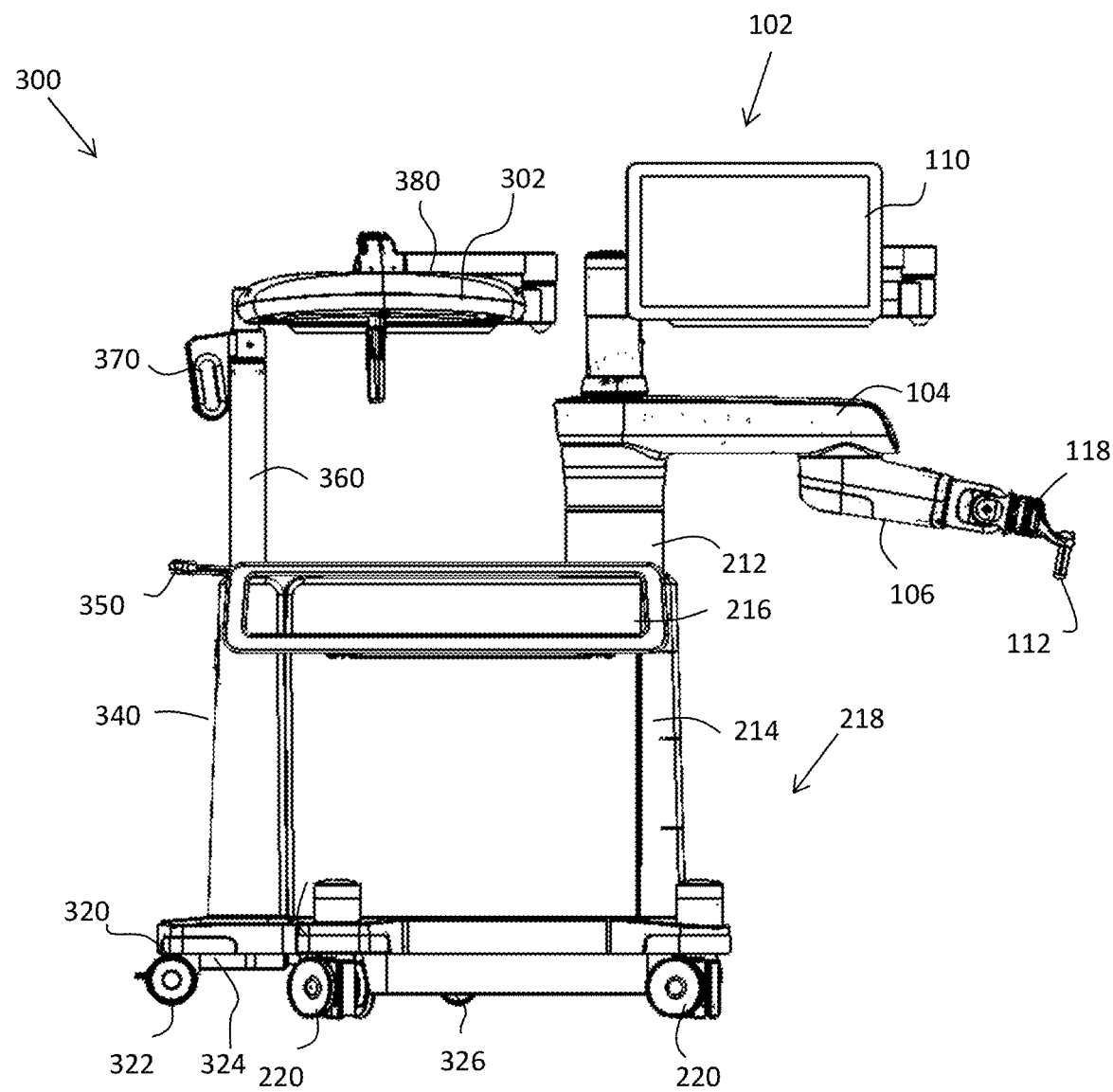
Figure 6:
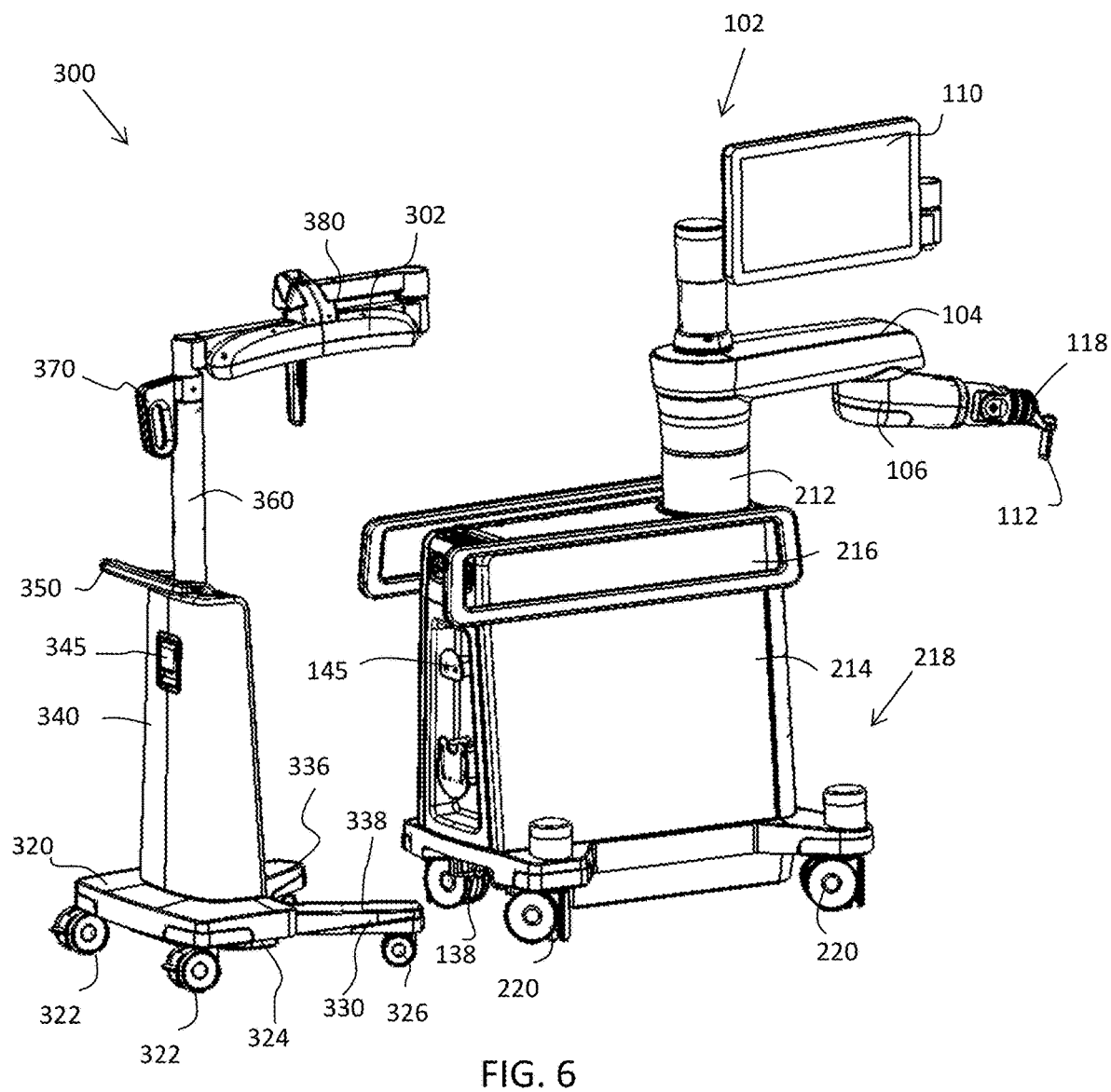
FIG. 6 illustrates the surgical robot with a deployed camera stand in accordance with an exemplary embodiment.

FIGS. 4 and 5 depict docking of the camera stand 300 with the surgical robot 102. In FIG. 4, handle 350 of the camera stand 300 is depressed to a roughly-horizontal position, which brings together the legs 336, 338 of the camera stand 300 (see FIG. 6). The user aligns the legs 336, 338 of the camera stand 300 with an opening 138 at the rear of the robot base, as also shown in FIG. 6, and pushes the camera stand 300 toward the robot 102. The legs engage rollers 136 internal to the robot base and the camera stand 300 is pushed up the ramp 130, including sloped portion 132 and level portion 134. When the camera stand 300 has fully engaged ramp 130, all the wheels or casters of the camera stand 300 are lifted off the floor, as depicted in FIG. 5. The forward portion or legs of the camera stand 300 have been maneuvered into the surgical robot 102, with front caster 326 visible below surgical robot base 218. Note the elevation of front caster 326 above casters or wheels 220 of the surgical robot 102. In this situation, the front casters 326 of the camera stand 300 will be above the floor and will not contact the floor after docking. Docking is now completed, and rear caster 322 and front caster 326 are now supported by the robot base 218, above the floor.

A rear perspective of this embodiment is depicted in FIG. 6, in which the camera stand 300 is in a deployed situation, separate from the robot 102 and deployed for use in an operating theatre or other chosen venue. Note that handle 350 has been angled upwardly, per the upward-pointing arrow, causing separation of legs 336, 338 from each other. Legs 336, 338 of the camera stand 300, are deployed at an angle to each other. For example, the legs 336, 338 may be angled from about 30 to 90 degrees, about 30 to 60 degrees, about 30 to 45 degrees, about 45 to 60 degrees to one another, or another suitable angle to maintain the stability of the stand 300. Other angles may also be used, so long as the camera stand 300 is stable and does not interfere with operating room personnel. Note also latch handle 345 on the rear of the camera stand 300, useful in this embodiment for engaging the camera stand with latch 145 of the surgical robot 102 with a hook (not shown) on the inside area of the camera stand 300. Other embodiments shown later in this disclosure use handle 345 with a different mechanism to positively engage and lock the camera stand to the surgical robot 102. FIG. 6 may also be considered as the operating or deployment configuration of the camera stand 300 and surgical robot 102, as it may be used by medical professionals.

Another comprehensive view of an exemplary embodiment, camera stand 700, is depicted in FIGS. 7A-7C, depicting the deployed configuration, and also in FIGS. 8A-8C, depicting the docking configuration. In FIGS. 7A-7C, camera stand 700 has been undocked or released from a surgical robot. FIG. 7A depicts a front perspective view of camera stand 700, with camera 702, camera stand base 720, housing 740, docking handle 750, vertical column 760, and camera extensions control handle 770. Camera 702 is able to achieve separation from the surgical robot and may be more advantageously placed via articulable arms 780, 782, joined with a rotary joint 784, which allows relatively free rotation and placement of the arms 780, 782 and the camera 702 as desired. In this configuration, legs 736, 738 of camera stand base 720 are separated by an angle A, which may be from about 30 to 90 degrees, about 30 to 60 degrees, about 30 to 45 degrees, about 45 to 60 degrees to one another, or another suitable angle. The legs 736, 738 are thus separated or deployed by raising handle 750, which has been raised, see arrow B, also in FIG. 7C. FIG. 7B is a top or plan view of the camera stand 700, useful for planning purposes by medical professionals wishing to maximize use of the available floor space in a crowded operating room or other venue.

When the surgery or other event has been completed, the camera stand 700 will be prepared for docking to the surgical robot 102, as depicts in FIGS. 8A-8C. Note in FIGS. 8A, 8B, the legs 736, 738 of the camera stand 700 have been joined with no appreciable separation of legs 736, 738 and no angle between the legs 736, 738, as shown by arrows C. Although shown with the legs 736, 738 in contact with one another, it will be appreciated that the legs 736, 738 may be spaced apart or otherwise configured depending on the shape, design, and configuration of the respective legs 736, 738. In FIG. 8A, the docking handle 750 has been lowered, as shown by the downward-facing arrow D in FIG. 8C. The camera 702 and arms 780 and 782 may be placed as desired to expedite docking, so that they do not interfere with the operation of docking the camera stand 700 to the surgical robot 102.

Figures 9A, 9B:
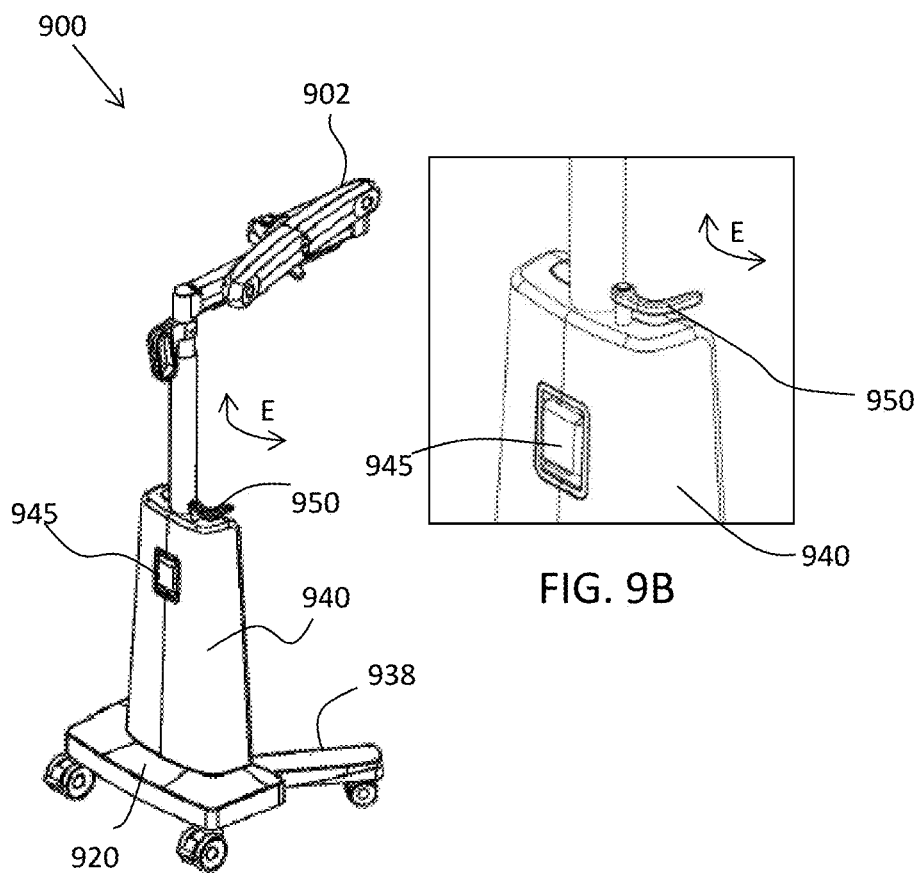
FIGS. 9A-9B depict an alternate embodiment of a deployed camera stand.

Several of the above-discussed embodiments have used handles 350 or 750, which require a vertical movement by the operator to spread or retract the legs of the camera stand. In other embodiments, as shown in FIG. 9A, camera stand 900 may include a handle 950 which is adapted to rotate in a horizontal plane, as shown by arrow E, to spread or retract the legs of the camera stand 900. Only right leg 938 is visible in FIG. 9A, the left leg hidden by the base 920 and cabinet 940 of the camera stand. Camera stand 900 also includes a camera 902, base 920 and latching handle 945. A closer view of the deployment handle 950 is seen in FIG. 9B. In this embodiment, the rotating or articulating legs described above are actuated by turning handle 950 at the top of the camera stand housing or cabinet in a horizontal plane, rather than by pushing a handle down. Internal gearing, not shown, may be used to amplify a mechanical advantage of the handle, allowing the user to close the legs and prepare the camera stand 900 for docking. The desired rotary motion may be achieved through a series of shafts, universal joints and gears. The legs may be locked in place via a spring-actuated locking pin. In one embodiment, the locking pin is released by the button on the handle, which is linked to the pin via a cable, such as a Bowden cable or other connecting mechanism.

Figure 10A:
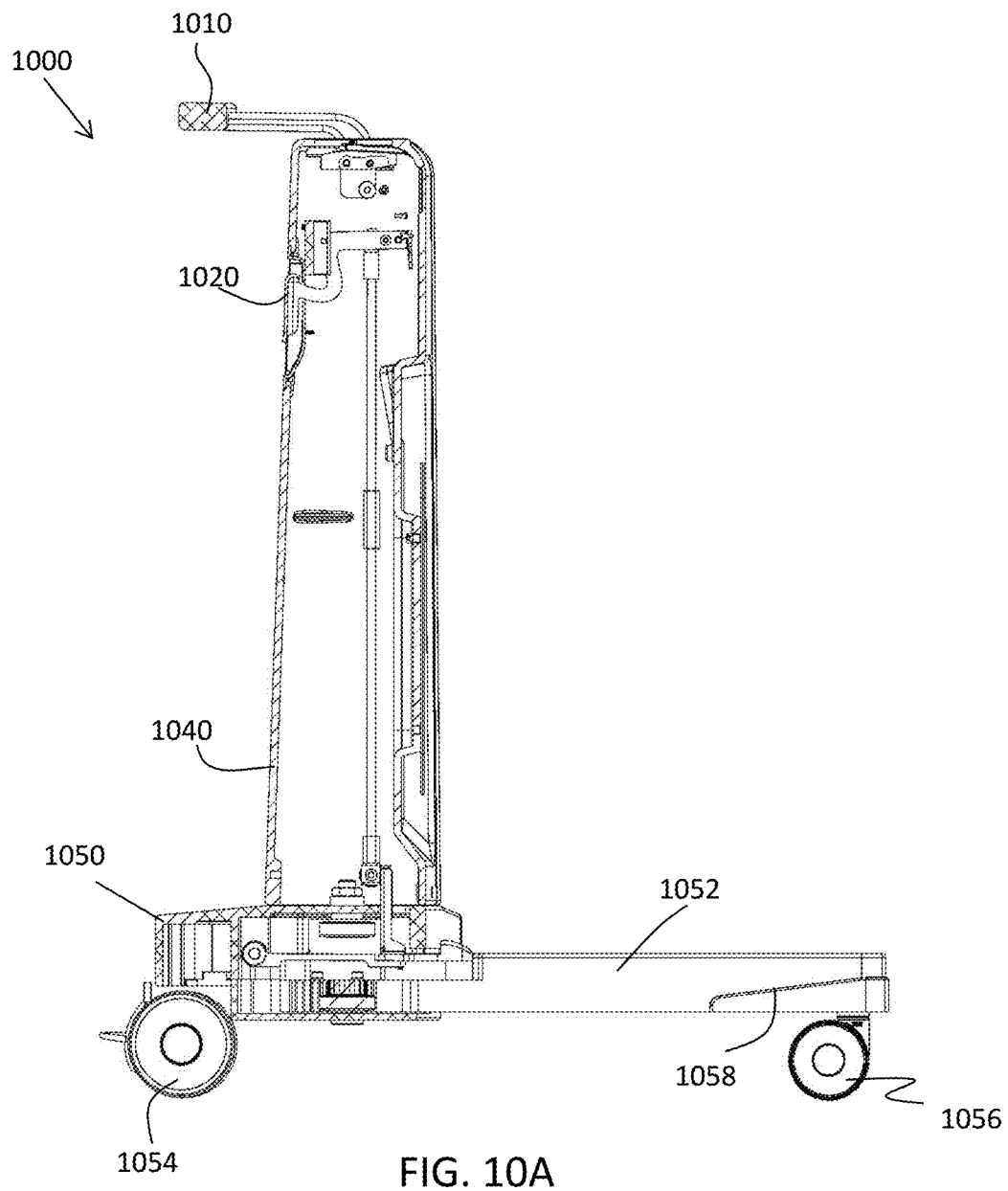
FIGS. 10A-10B depict internal parts of an embodiment of a dockable, deployable camera stand, in a docked configuration in accordance with the present disclosure.
Figure 10B:
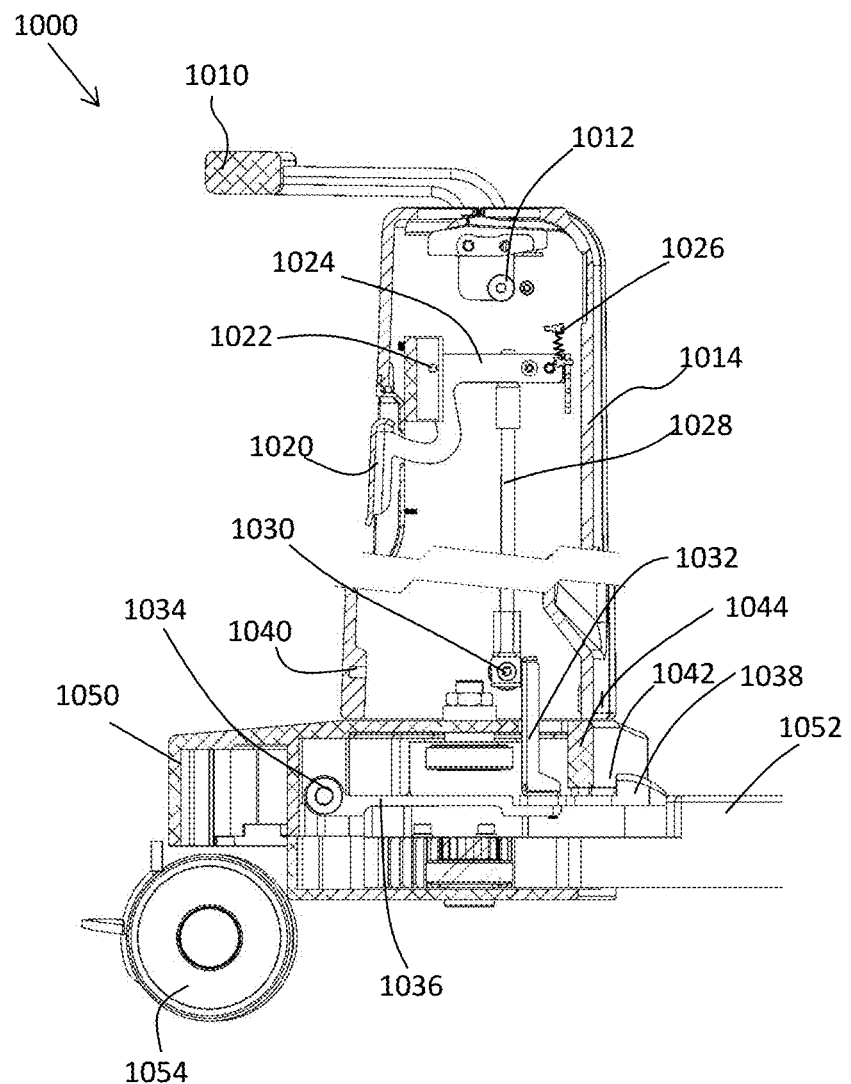
Figure 11:
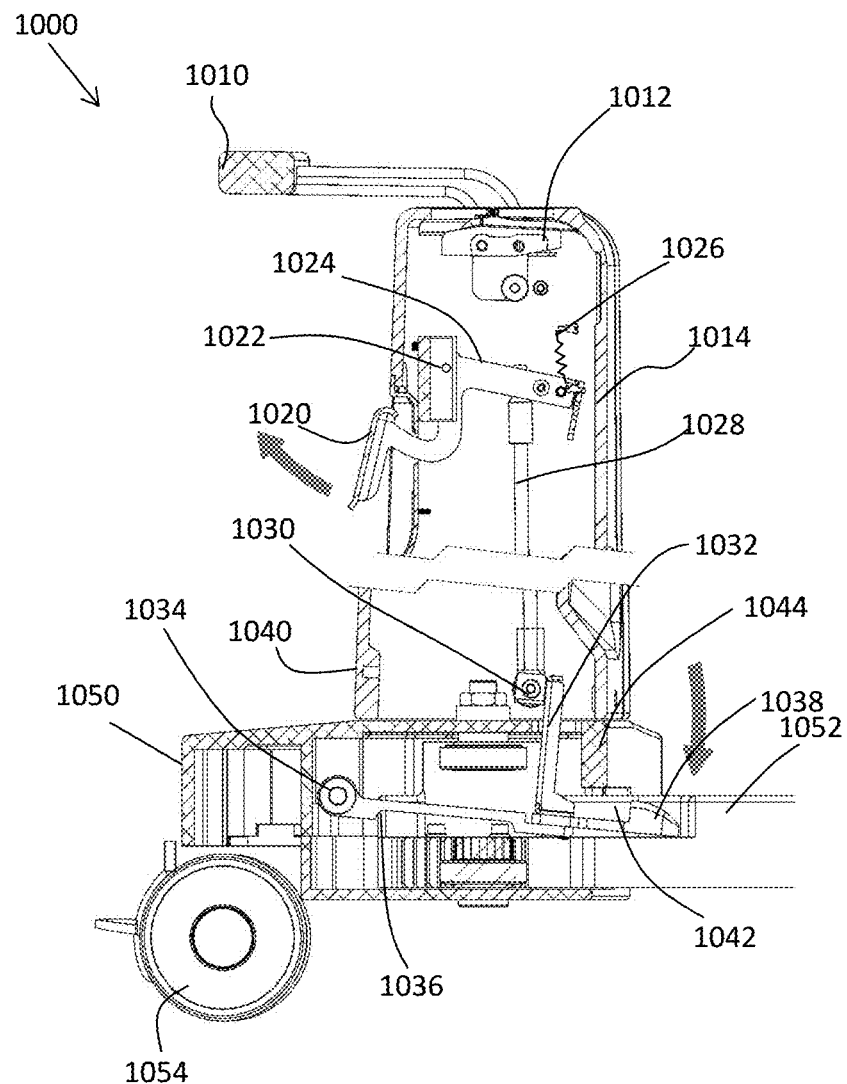
FIG. 11 depicts the dockable, deployable camera stand of FIGS. 10A-10B in moving to a deployable configuration.

FIGS. 10A-16 depict more detailed views of the hardware and mechanisms that may be used in a camera stand as described in this disclosure. As noted, above, simpler mechanisms may be used. FIGS. 10A, 10B and 11 depict one embodiment in which a latching pawl is used to positively secure the camera stand 1000 to the surgical robot 102. In these views, only the camera stand 1000 is depicted; it is understood, therefore, that in embodiments, when the camera stand 1000 is docked and latch to the surgical robot, the camera stand 1000 is suspended with its casters off the floor. It is also understood that the latching pawl, as described herein, fits into a corresponding space of the surgical robot for positive retention. The latching pawl is at a far end, or distal end of a lever of which it forms a part.

FIGS. 10A-10B depicts a camera stand 1000 for docking with and deployment from a surgical robot. As seen in FIG. 10A, camera stand 1000 includes a cabinet 1040 and a base 1050, base 1050 including legs 1052 (only one leg visible), rear caster 1054 and front caster 1056. Ramp 1058 is an embodiment of the ramp previously discussed, allowing upward movement of the camera stand when docking to a surgical robot or other main system. Handles include deployment handle 1010 and paddle handle 1020. Addition details are depicted in FIG. 10B. Deployment handle 1010 is connected to deployment mechanism 1012 and connecting rod 1014 to additional mechanisms near the base of the camera stand. Paddle handle 1020 is mounted to the internal portions of cabinet 1040 via handle pivot 1022. Handle pivot 1022 is connected via lever 1024 to a retaining spring 1026, which resists upward movement of paddle handle 1020 and also resists downward movement of connecting rod 1028. Connected rod 1028 connects to linkage 1030, then through bracket 1032. Bracket 1032 connects to lever 1036, pawl pivot 1034 and pawl 1038. Pawl 1038 is depicted in FIG. 10B in an upward position. Pawl 1038 is a retainer for locking the camera stand to the surgical robot. Pawl 1038 includes a right-angle portion 1042. The right angle portion 1042 is spaced apart from an internal support 1044 of the camera stand. When camera stand 1000 is docked to a surgical robot, the right-angle portion 1042 of the pawl 1038 captures a portion of the surgical robot (not shown) in the space between the right-angle portion 1042 and internal support or wall 1044.

When the surgical robot and camera stand are to be used, the camera stand 1000 is deployed, as shown in FIG. 11. In this situation, paddle handle 1020 is raised by pulling on the handle. When the handle is raised, lever 1024 pivots on pivot 1022 overcoming the force of spring 1026 and lowering the connecting rod 1028, linkage 1030 and bracket 1032. This causes clockwise pivoting of lever 1036 on pivot 1034, lowering the pawl 1038 and releasing the camera stand from the surgical robot. Note that in FIG. 11, right-angle portion 1042 of pawl 1038 is more easily seen. In short, the camera stand is deployed by pulling up on the paddle handle to release the locking latch or pawl 1038. At this point, the camera stand can be rolled down the ramp by the user until the camera legs are completely outside the robot base. When the legs are no longer constrained by the robot base, the internal gas spring 1240 exerts a downward force to automatically spread or deploy the legs. This could also be accomplished with a compressed coil or torsion spring. As also explained below, the legs are automatically locked in the open position by the lower pivoting mechanism 1250. Thus, FIGS. 10A, 10B and 11 show an exemplary embodiment of how the camera stand is positively latched to the surgical robot and is released from the surgical robot.

Figure 13:
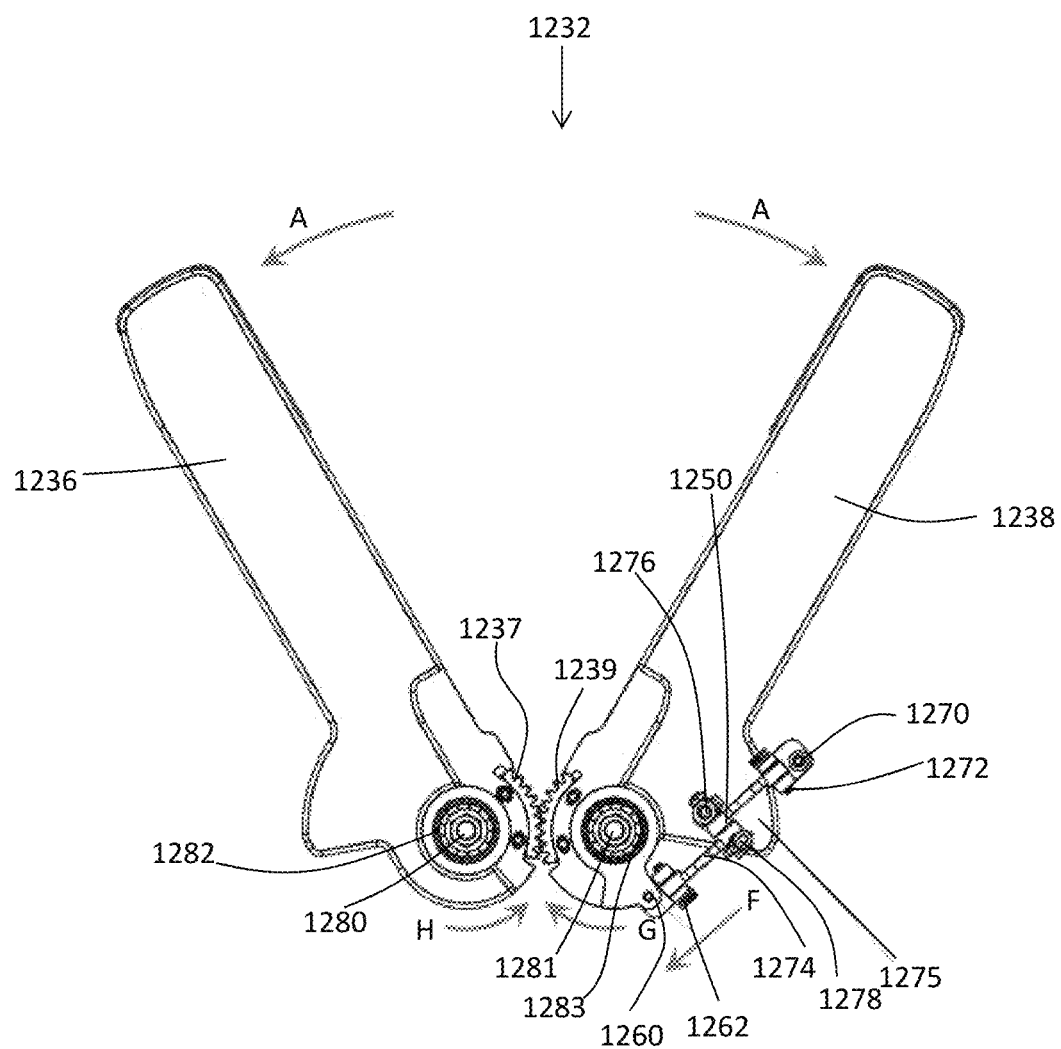
FIG. 13 depicts internal details of the camera stand of FIGS. 12A-12B as an operator moves to close the articulating legs and dock the camera stand.

One embodiment of a leg-deploying mechanism is depicted in FIGS. 12A, 12B and 13. In FIG. 12A, a leg-deploying mechanism 1200 of a camera stand includes a deploying handle 1210, upper pivoting mechanism 1212, upper linkage 1220, a connecting rod 1230 and a lower pivoting mechanism 1250. Additional details of mechanism 1200 are depicted in FIG. 12B, which depicts deploying handle 1210 in a raised configuration. As discussed with other embodiments, deploying handle 1210 is raised to separate the legs of the camera stand and to deploy the camera stand.

When deploying handle 1210 is raised, as shown by the upward arrow near handle 1210, mechanism 1212 causes pivoting of upper linkage 1220 and lowering of connecting rod 1230, as shown by the downward arrow near mechanism 1212. When the connecting rod 1230 is forced down, lower pivoting mechanism 1250 is also forced down. The lower pivoting mechanism includes connections 1260, 1270 to different portions of a single leg of the camera stand. The connections include pivoting points 1262, 1272 which are connected to lower pivoting mechanism 1250 as shown, by levers 1274, 1275. Lower pivoting mechanism 1250 connects to connecting rod 1230 via mount 1276 and it also connects to gas spring 1240 via mount 1278. Mounts 1276, 1278 may be made via pins, threaded fittings or any convenient and useful mechanical connection.

When the user raises handle 1210 to deploy the camera stand, the downward thrust of connecting rod 1230 through mount or connector 1276 to lower the lower linkage pivoting mechanism 1250 may be assisted by optional gas spring 1240, shown by the downward arrow near the gas spring 1240, which also presses down on the lower pivoting mechanism 1250 through mount 1278. The gas spring provides a force to move the lower pivoting mechanism inwardly and open the legs of the camera mount. The force provided by the gas piston also provides a stabilizing and constant force to keep the legs open. Both the connecting rod 1230 and the spring 1240 may be considered components that convert linear motion, their downward motion, into rotary motion for deploying the legs of the camera stand.

Later, when one desires to dock the camera stand 1000, the connecting rod may be lifted, by lowering the handle 1210, thus converting upward linear motion of the connecting to an opposite rotary motion for closing the legs of the camera stand.

As shown in FIG. 12B, raising handle 1210 to deploy the camera stand has the effect of pivoting levers 1274, 1275 through pivot points 1262, 1272, thus forcing the levers downward and outward. The effect on legs 1236, 1238 of the camera mount is explained with reference to FIGS. 12B and 13. The arrows in FIG. 13 summarize the movements. When force is downwardly applied through the connecting rod 1230 or gas spring 1240 to mounts 1276, 1278, the lower pivoting mechanism tends to move downward and inwardly, as shown by arrow F in FIG. 13. This causes clockwise rotation of right leg 1238 about its bearing 1283 and bearing center 1281, as shown by arrow G through gear sector 1239. Matching gear sector 1237 on left leg 1236 then rotates counterclock-wise, as shown by arrow H, and opens legs 1236. 1238 at their far ends, shown by arrows A. The bearings 1282, 1283 and their centers 1280, 1281 act as pivot points for rotating the legs, causing the legs to deploy in FIG. 13. Movement in the opposite direction, as shown in FIG. 14B, causes the legs to close. The wider portions of the legs, just above gear sectors 1237, 1239, act as a hard stop for closing movements of the legs and also for horizontal and vertical movement of the lower pivoting mechanism.

The force applied to lower pivoting mechanism 1250 is transmitted to left and right pivot points 1262, 1272, which are anchored to right leg 1238 respectively via connections 1260, 1270. We now consider the force applied to right leg 1238 by forces applied through pivoting mechanism 1250 along an imaginary line extending through connection 1260, left pivot 1262, levers 1274, 1275, right pivot 1272 and connections 1270. Along this imaginary line, left pivot point 1262 is aligned with right leg 1238 bearing 1283 and bearing center 1281, while right pivot point 1272, however, is much further away from the right leg bearing 1283 and its center 1281. There is very little distance along the imaginary line between bearing center 1282 and left pivot 1262, while there is a much greater distance along the line between bearing center 1282 and right pivot 1272. When force is applied to lower pivoting mechanism 1250, there is very little moment applied to leg 1238 through left pivot 1262 and connection 1260, while there is a much larger moment, force through a distance, applied through right pivot 1272 and connection 1270. As a result, pivoting mechanism 1250 moves downwardly, as indicated in FIG. 12B. Left pivot 1262 and right pivot 1272 also move downwardly. Since left pivot 1262 is aligned with bearing center 1281, it is constrained and rotates very little with respect to bearing center 1281, but right pivot 1272 acts at a greater distance along the imaginary line, applying a force at connection point 1270, thus rotating right leg 1238 through right bearing 1283 and its center 1281.

In this example, legs 1236, 1238 are mounted to the camera stand base, as shown, for example, in FIGS. 10A 10B and 11. The legs 1236, 1238 are mounted on centers 1280, 1281 with bearings 1282, 1283, respectively, for rotation about the centers 1280, 1281. Lower pivoting mechanism 1250 is connected, in this embodiment, to right leg 1238 via connections 1260, 1270 through levers 1274, 1275 and pivot points 1262, 1272. Pivot points 1262, and 1272 are non-symmetric with respect to bearing center 1281 of the right leg 1238. Therefore, when force is downwardly applied through the connecting rod 1230 or gas spring 1240, to mounts 1276, 1278, the forces applied to leg 1238 through connections 1260, 1270, causes unequal moments, force acting through a distance, to be applied to the points of connection, e.g., less moment to point 1260 and greater moment to point 1270. These unequal moments cause rotation of right leg 1238 and a slight inward movement of the lower pivoting mechanism 1250, with right leg 1238 rotating clockwise on its bearing 1283 and bearing center 1281. This opens right leg 1238. Right leg 1238 includes a gear sector 1239 connected to a gear sector on left leg 1236, which also opens, with equal gears, an equal amount, rotating counterclockwise. Left leg is also mounted to the camera stand base with a bearing 1282 and center point 1280. The legs may be designed for equal movement. In one embodiment, the linkage is pushed downward so that an angle of greater than 180 degrees is formed between levers 1274, 1275. This linkage may thus be termed a past center mechanism. In this configuration, the legs 1236, 1238 are locked in position and cannot be moved until either the gas spring or the handle is actuated to lift the lower pivoting mechanism.

In one embodiment, the deploying mechanism discussed above is combined with the paddle handle locking latch or pawl discussed above with respect to FIGS. 10A-10B. In this embodiment, a camera stand is deployed by pulling up on the paddle handle 1020 on the rear of the camera stand housing or cabinet, to release the locking latch or pawl 1038, as shown in FIG. 11. At this point, the camera stand can be rolled down the ramp by the user until the camera legs are completely outside the robot base. When the legs are no longer constrained by the robot base, the internal gas spring 1240 exerts a downward force to automatically spread or deploy the legs. As also explained below, the legs are automatically locked in the open position by the lower pivoting mechanism 1250, which may be termed a past-center mechanism. The benefit of this type of mechanism is that locking requires no further action by the user, and the legs themselves cannot be closed by applying a force to the legs. Only by lifting the handle can the past-center mechanism or lower-pivoting mechanism 1250 be activated to reverse its motion.

Figure 14A:
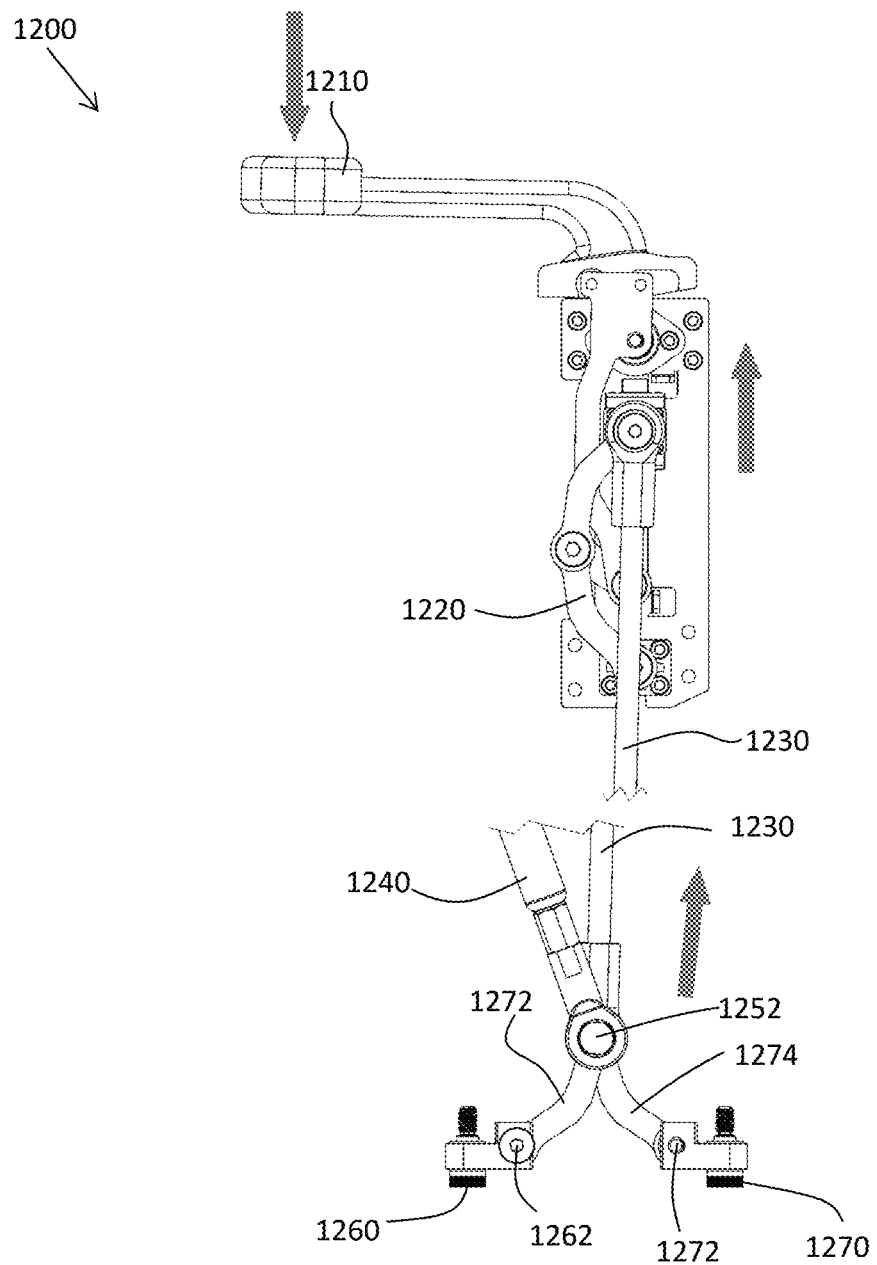
FIGS. 14A-14B depicts internal details of the articulating legs of the camera stand, illustrating how deploying and docking movements are made.
Figure 14B:
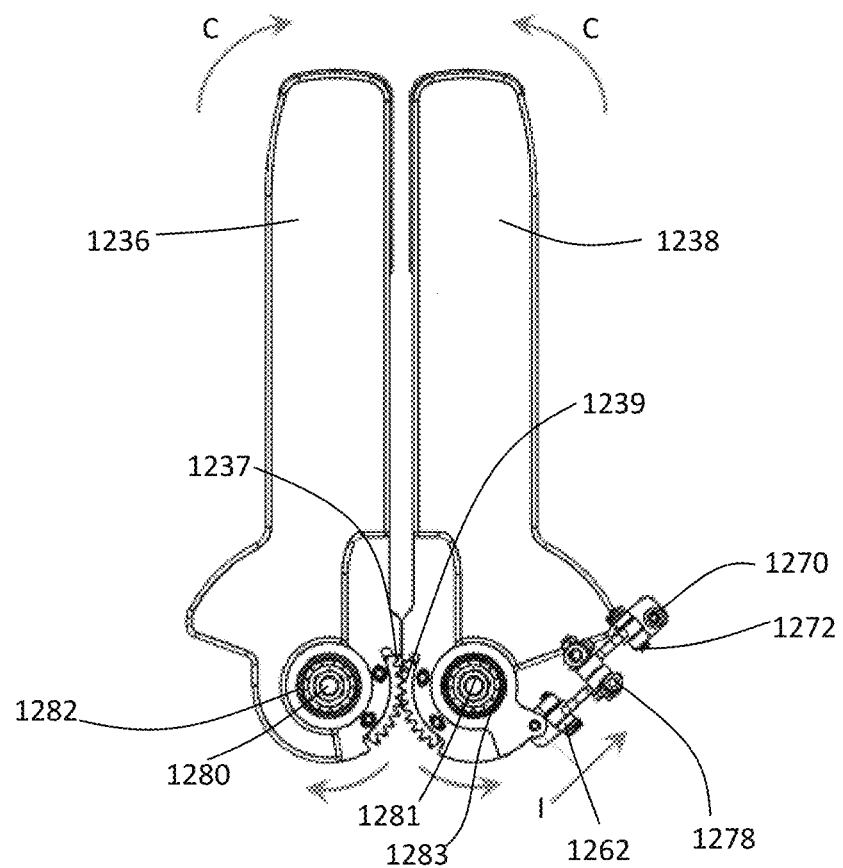

In order to close the legs and prepare the camera mount for docking, mechanism 1200, as shown in FIG. 14A, is used for the reverse of the process just discussed. Handle 1210 is lowered, as shown by the downward arrow, thus raising the connecting rod 1230 through mechanism 1220, as shown by the two upward arrows. This movement may be opposed by gas spring 1240. When the connecting rod 1230 is raised, lower pivoting mechanism 1250 is also raised, thus raising levers 1271, 1274 and causing outward movement in the direction of arrow I. This is also shown in FIG. 14B, with outward movement I causing counter-clockwise movement of gear sector 1239 and counter-clockwise (closing) movement of right leg 1238. Left leg 1236 is connected through its gear sector 1237, which rotates an equal amount in a clockwise direction, resulting in a clockwise, closing movement of left leg 1236. With the legs closed, the camera mount is ready for docking.

Figure 15:
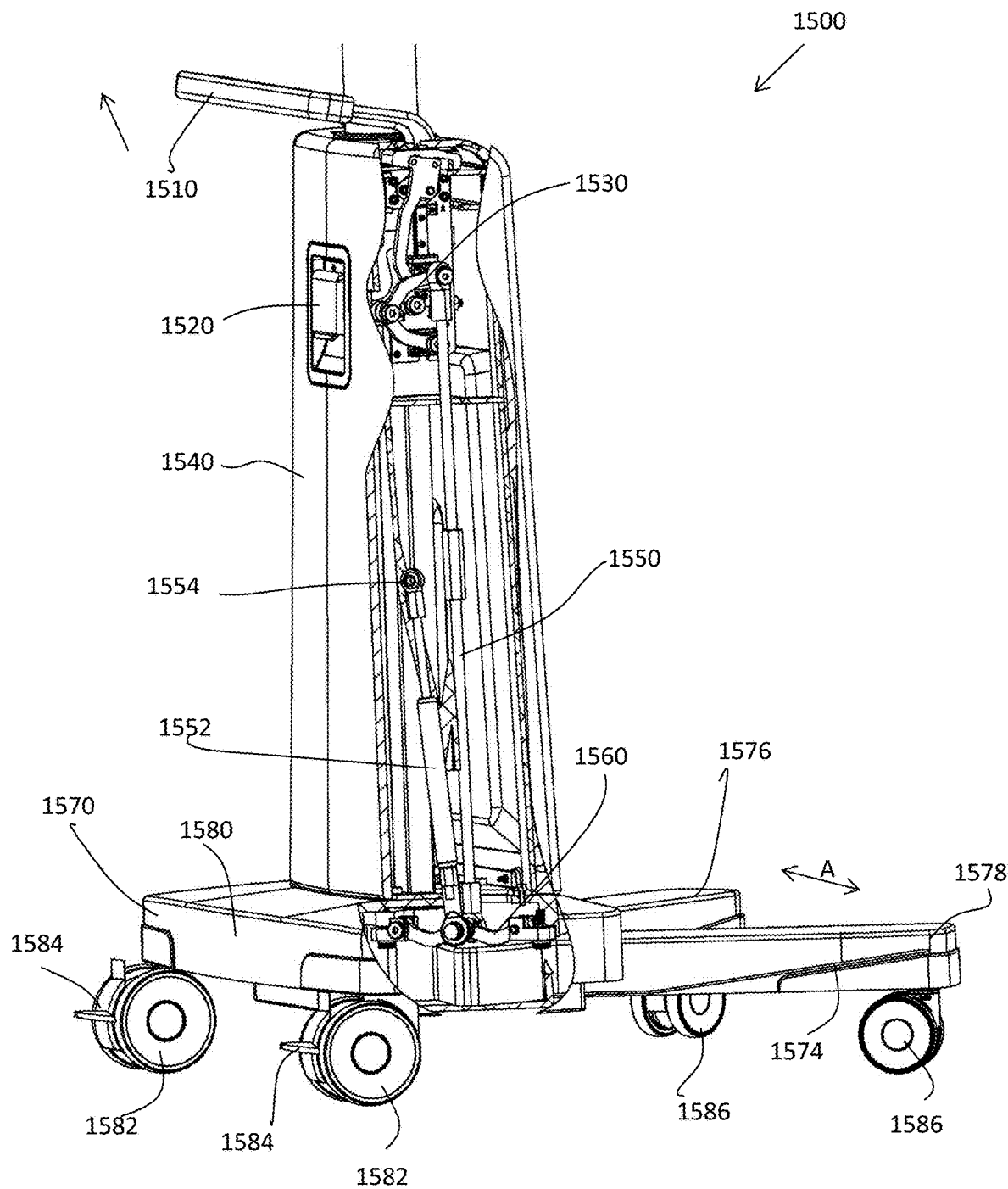
FIG. 15 depicts a rear perspective, partially broken-open view of the camera stand of FIGS. 13, 14A and 14B as the operator moves the camera stand to a deployed configuration.
Figure 16:
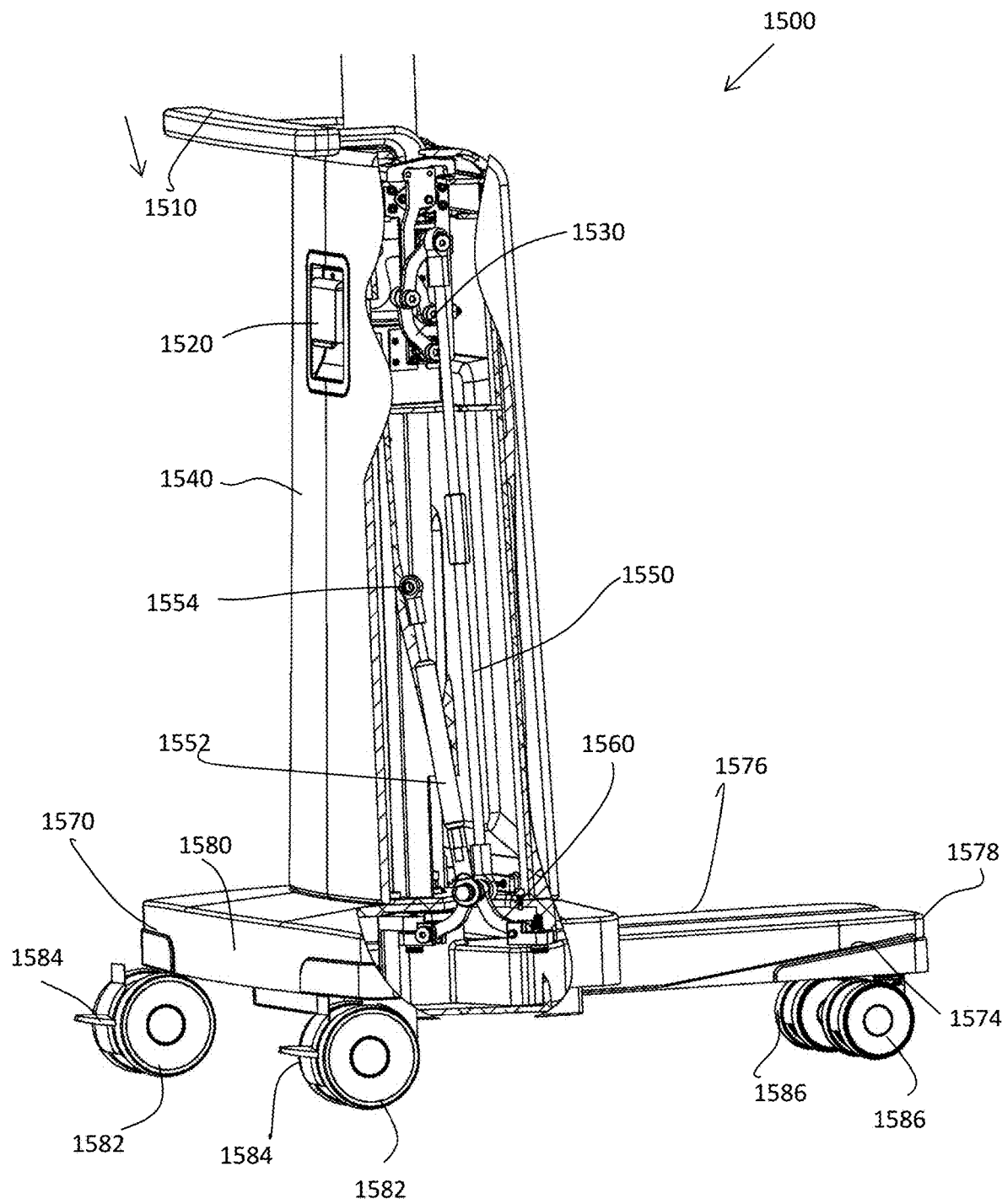
FIG. 16 illustrates the camera stand of FIG. 15 as the operator moves to a docking configuration.

Overall views of the camera stand are disclosed in FIGS. 15 and 16, which disclose respectively, a deployed configuration of the camera stand 1500 and a docking configuration of the camera stand. Both FIGS. 15 and 16 present side, broken-out perspective views of the camera stand, partially revealing the internal mechanisms. In FIG. 15, camera stand 1500 includes a first handle 1510, a second docking or paddle handle 1520, a cabinet or housing 1540 and a base 1570 with a lower platform 1580. Base 1570 includes left and right legs 1576, 1578, separated by angle A, as shown.

Base 1570 includes rear casters 1582 with locks 1584 as well as front casters 1586 (only one visible in FIG. 15). Ramp 1574 is a sloped portion on the right side of the right leg 1578, as shown, with a matching ramp, not visible in FIG. 15, on the left side of left leg 1576, to assist in docking the camera stand to a surgical robot.

Camera stand 1500, in FIG. 15 discloses a first deploying/docking handle 1510. In FIG. 15, handle 1510 has been raised, as shown by the arrow near handle 1510. As shown in the partly-broken-open views, raising handle 1520 causes downward motion of connecting rod 1550, optionally assisted by gas spring 1552. Either of both of these result in linear, downward movement of lower linkage 1560. As explained with respect to FIGS. 12A, 12B and 13, this results in inward movement of the lower linkage 1560 and an opening motion for legs 1576, 1578. The reverse holds for FIG. 16, in which the movements are reversed, using the same camera stand 1500 and the same components. Handle 1510 is lowered, as shown by the downward-facing arrow near handle 1510. This raises the connecting rod 1550, and if a gas spring 1552 is used, overcomes the downward force of the gas spring on lower linkage 1560. Lower linkage 1560 is also raised resulting in outward movement of the lower linkage and a closing motion of the legs, as discussed with respect to FIGS. 14A, 14B.

There are many benefits and advantages to the articulating or dockable camera stand as disclosed herein. A principal benefit is that the articulating camera stand allows for much better viewing and observation of the operating field. The position of the camera can be chosen to fit the patient, the procedure and the particular venue or operating room in use. Another benefit is that the camera stand base can be easily arranged in either a deployed configuration or a docking configuration. Changing from the deployed to the docking configuration requires only one action, e.g., pushing down on the principal operating handle. The ability of the camera stand to dock with the surgical robot or other main system allows for both pieces of equipment to be manipulated simultaneously for transport and storage while maintaining a minimal overall system footprint. In addition, the camera stand and its casters are lifted off the ground while the system is docked, which affords improved maneuverability during transport.

Undocking the camera stand requires only one action from the user, and when the camera stand is fully undocked, the articulating legs automatically deploy and lock in the open position without further action from the user. The past-center locking mechanism prevents the legs from being back-driven by forces applied to the legs. This means that the legs will not close from inadvertent bumping of the legs, or from intentional attempts to close the legs by pushing them shut. The legs can only be closed by intentionally actuating the handle, e.g., by pulling up on the handle, as described. This ensures that the legs remain in the open, stable position while the camera stand is deployed.

There are many other embodiments of the present disclosure. For example, only standard, non-powered wheels and casters have been discussed. In other embodiments, the camera stand may dock with the surgical robot with the wheels or casters remaining on the ground. Once the camera stand latches to the robot or other main system, the camera stand casters may be lifted up by a lead screw. This may be accomplished, for example, by servo motors or stepper motors. In some embodiments described herein, the surgical robot includes rollers to assist with the docking. In other embodiments, rollers or rolling elements may be incorporated into the camera stand legs and used to roll the camera stand into the internal portions of the robot or main system. In these embodiments, the user may still manually roll the camera stand up the ramp profile for docking. In other embodiments, as partly shown in FIG. 6, the camera stand is rolled into a docking position near a surgical robot or other main system. An internal latch actuated by a latch handle 345 may be used to actuate a lever to lift the camera stand onto the main system, which is then locked in place. The lever should have sufficient mechanical advantage to allow easy lifting of the weight of the camera stand by the user.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference, as if each such patent or publication were individually incorporated by reference herein. Various features and advantages of the invention are set forth in the following claims.

What is claimed is:

1. A surgical robot system comprising:
   a surgical robot having a robot base and a robot arm coupled to the robot base; and
   a camera stand for mounting a camera, the camera stand including a base with casters, a housing, a camera-mounting portion, and at least one control handle configured to secure the camera stand to the robot and for releasing the camera stand from the robot
   wherein the camera stand includes a pivoting lever linked to the at least one control handle for securing the camera stand to the robot and for releasing the camera stand from the robot,
   wherein raising the control handle forces the pivoting lever through pivot points to deploy the camera stand.

2. The surgical robot system of claim 1, wherein the camera stand base comprises a sloped ramp, the camera stand is secured to the robot base via the sloped ramp of the camera stand base and a sloped ramp on inner portions of the robot base.

3. The surgical robot system of claim 1, wherein the at least one control handle further comprises a second handle for assisting in deploying and retracting legs of the camera stand base.

4. The surgical robot system of claim 3, wherein the legs of the camera stand comprise a left leg pivotally mounted to the base of the camera stand via a left leg pivot and a right leg pivotally mounted to the base of the camera stand via a right leg pivot.

5. The surgical robot system of claim 1, wherein the pivoting lever further comprises a pawl at a distal end of the pivoting lever, the pawl adapted to fit into a space in the robot base to secure the pawl and to secure the camera stand to the camera base.

6. The surgical robot system of claim 3, wherein the camera stand is adapted, via movement of the second handle, to convert linear motion of a connecting rod or spring of the camera stand to rotary motion of the legs of the camera stand.

7. The surgical robot system of claim 6, further comprising a pivoting mechanism connected to the connecting rod or spring, the pivoting mechanism comprising a central pivot, a left pivot and a right pivot, the left and right pivots connected to a single leg of the camera stand, wherein linear motion of the connecting rod or spring causes pivoting of the central pivot with respect to the left and right pivots.

8. The surgical robot system of claim 7, wherein pivoting of the central pivot via the connecting rod or spring causes vertical movement of the central pivot and causes rotational movement of legs of the camera stand.

9. The surgical robot system of claim 7, wherein the left and right pivots are connected to the single leg of the camera stand via different moment arms of the left and right pivots with respect to the single leg of the camera stand.

10. The robot surgical system of claim 1, further comprising at least one camera adapted to mount on the camera-mounting portion of the camera stand, the camera adapted to detect a plurality of tracking markers mounted on at least one of: the robot arm; an end-effector of the robot arm; a tool of the end effector; and a patient, wherein the robot and the at least one camera are adapted to determine a 3-dimensional position of the robot arm, the end-effector, the tool or the patient via one or more of the plurality of tracking markers.

11. The robot surgical system of claim 1, further comprising a plurality of tracking markers to be mounted on at least one of: an end-effector of the robot arm; a tool of the end effector; and a patient, wherein the one or more tracking markers are active markers having an active state and an inactive state, the active state emitting an infrared signal detected by the at least one camera, and the inactive state not emitting the infrared signal such that the one or more tracking markers are not detected by the at least one camera.

12. A surgical robot system comprising:
   a surgical robot having a robot base and a robot arm coupled to the robot base, the robot base including a lifting mechanism; and
   a camera stand for mounting a camera, the camera stand including a base with casters, a housing, a camera-mounting portion, and a first control handle configured to secure the camera stand to the robot and for releasing the camera stand from the robot,
   wherein the camera stand includes two legs, each leg configured for mounting the camera stand with the lifting mechanism of the robot base
   wherein the camera stand comprises a pivoting lever linked to the first control handle for securing the camera stand to the robot and a second control handle for deploying the two legs of the camera stand.

13. The surgical robot system of claim 12, wherein the pivoting lever further comprises a pawl at a distal end of the pivoting lever, the pawl adapted for fit into a space in the robot base to secure the pawl and the camera stand to the camera base.

14. The surgical robot system of claim 12, wherein the camera stand is adapted, via movement of the second handle, to convert linear motion of a component of the camera stand to rotary motion of the legs of the camera stand.

15. The surgical robot system of claim 14, further comprising a pivoting mechanism connected to the component, the pivoting mechanism comprising a central pivot, a left pivot and a right pivot, the left and right pivots connected to a single leg of the camera stand, wherein linear motion of the component causes pivoting of the central pivot with respect to the left and right pivots.

16. The surgical robot system of claim 15, wherein the component comprises a connecting rod or a spring connected to the pivoting mechanism, the connecting or the spring adapted to assist in deploying the two legs of the camera stand.

17. The surgical robot system of claim 15, wherein pivoting of the central pivot via the component causes vertical movement of the central pivot and causes horizontal motion of the left and right pivots.

18. The surgical robot system of claim 15, wherein the left and right pivots are connected to the single leg of the camera stand via different moment arms of the left and right pivots with respect to the right leg pivot of the camera stand.

* * * * *